United States Patent

Kobayashi et al.

[11] Patent Number: 5,488,182
[45] Date of Patent: Jan. 30, 1996

[54] PHENOL COMPOUNDS CONTAINING METHOXYMETHYL GROUP OR HYDROXYMETHYL GROUP

[75] Inventors: Fumikazu Kobayashi; Kazuyoshi Mizutani; Kazuo Maemoto, all of Shizuoka, Japan

[73] Assignee: Fuji Photo Film Co., Ltd., Kanagawa, Japan

[21] Appl. No.: 269,040

[22] Filed: Jun. 30, 1994

[30] Foreign Application Priority Data

| Jun. 30, 1993 | [JP] | Japan | 5-161256 |
| Aug. 9, 1993 | [JP] | Japan | 5-197474 |
| Aug. 24, 1993 | [JP] | Japan | 5-209170 |

[51] Int. Cl.$^6$ .................................................. C07C 39/16
[52] U.S. Cl. ................................................ 568/660; 568/720
[58] Field of Search .................................. 568/660, 720

[56] References Cited

U.S. PATENT DOCUMENTS

| 3,941,850 | 3/1976 | Brindell et al. | 568/720 |
| 4,387,152 | 6/1983 | Stahlhofen | 430/191 |
| 4,778,936 | 10/1988 | Mizuno et al. | 568/720 |

FOREIGN PATENT DOCUMENTS

| 0050802 | 5/1982 | European Pat. Off. | 568/660 |
| 0416544 | 3/1991 | European Pat. Off. | 568/720 |
| 0443820 | 8/1991 | European Pat. Off. | 568/720 |
| 0530148 | 3/1993 | European Pat. Off. | 568/720 |
| 0542572 | 5/1993 | European Pat. Off. | 568/660 |

OTHER PUBLICATIONS

Mark, Chem. Abst., vol. 94, #140,421d (1981).

*Primary Examiner*—James H. Reamer
*Attorney, Agent, or Firm*—Sughrue, Mion, Zinn, Macpeak & Seas

[57] ABSTRACT

A novel methoxymethyl- or hydroxymethyl-containing phenol compound represented by the following formula (I), (II), (III), (IV) or (V) is disclosed:

(Abstract continued on next page.)

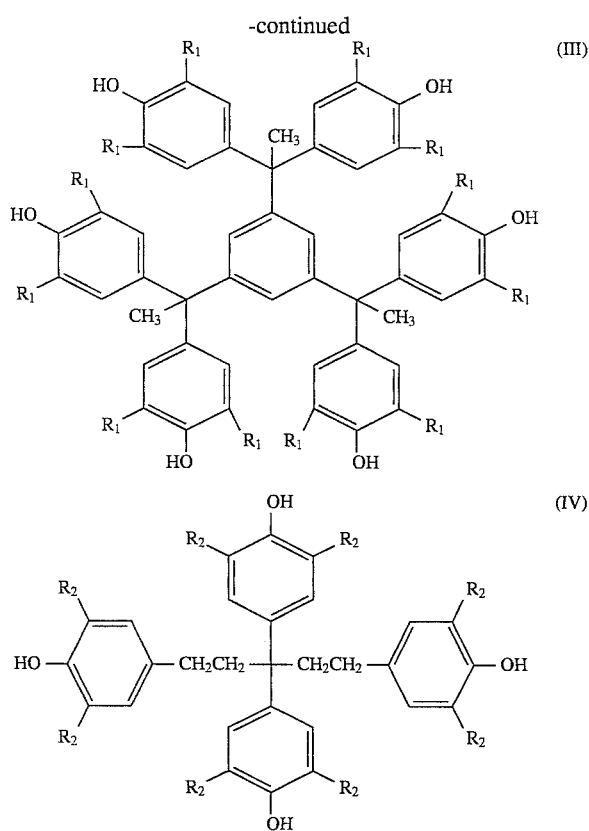
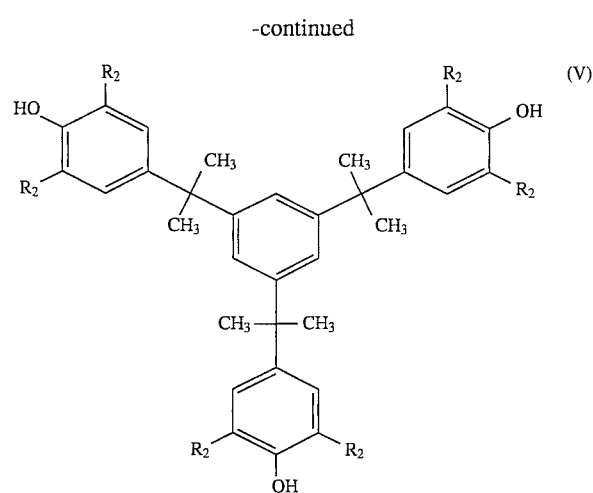
wherein each R represents $CH_2OCH_3$, $CH_2OH$, or H, provided that at least three of the R's are $CH_2OCH_3$ or $CH_2OH$, with at least one thereof being $CH_2OCH_3$; each $R_1$ represents $CH_2OCH_3$, $CH_2OH$, or H, provided that at least two of the $R_1$'s are $CH_2OH$; and each $R_2$ represents $CH_2OCH_3$, $CH_2OH$, or H, provided that at least two of the $R_2$'S are $CH_2OH$.
5 Claims, No Drawings

PHENOL COMPOUNDS CONTAINING METHOXYMETHYL GROUP OR HYDROXYMETHYL GROUP

FIELD OF THE INVENTION

The present invention relates to novel phenol compounds containing a methoxymethyl group or a hydroxymethyl group.

BACKGROUND OF THE INVENTION

It has conventionally been known that hydroxymethyl-containing phenol compounds are used in various applications. For example, besides being applied to coating compositions as described in "THE CHEMISTRY OF ORGANIC FILM FORMERS" written by D. H. Solomon, hydroxymethyl-containing phenol compounds are used in many fields such as, e.g., lithographic plates, photoresists, adhesives, molding materials, laminating materials, and binders.

Frequently used in these applications are a phenol-formaldehyde-resol resin or the compounds described in Japanese patent publication (examined) No. Hei-1-49932, specifically such compounds as bishydroxymethyl-p-cresol and tetrakis(hydroxymethyl)bisphenol A.

However, such conventionally known hydroxymethyl-containing phenol compounds have been disadvantageous in that methylol groups, which function as a crosslinking group, cannot be incorporated in the molecule in a large number. The phenol-formalin-resol resin also is disadvantageous in that the number of the reactive hydroxymethyl groups contained in the molecule is small. Hence, both the hydroxymethyl-containing phenol compounds and the phenol-formaldehyde-resol resin have failed to attain sufficient cured-film performances when used in coating compositions, photosensitive printing plates, etc. It has therefore been necessary that in order to meet cured-film performance requirements, the hydroxymethyl-containing phenol compounds or the resol resin should be incorporated in a large amount.

Further, there has been another problem that the incorporation of a hydroxymethyl group results in impaired solvent solubility.

SUMMARY OF THE INVENTION

Accordingly, an object of the present invention is to provide a methoxymethyl- or hydroxymethyl-containing phenol compound which has sufficient cured-film performances even when used in a smaller amount as compared with the conventional hydroxymethyl-containing phenol compounds and resol resin.

The methoxymethyl- or hydroxymethyl-containing phenol compound of the present invention is represented by the following formula (I), (II), (III), (IV) or (V):

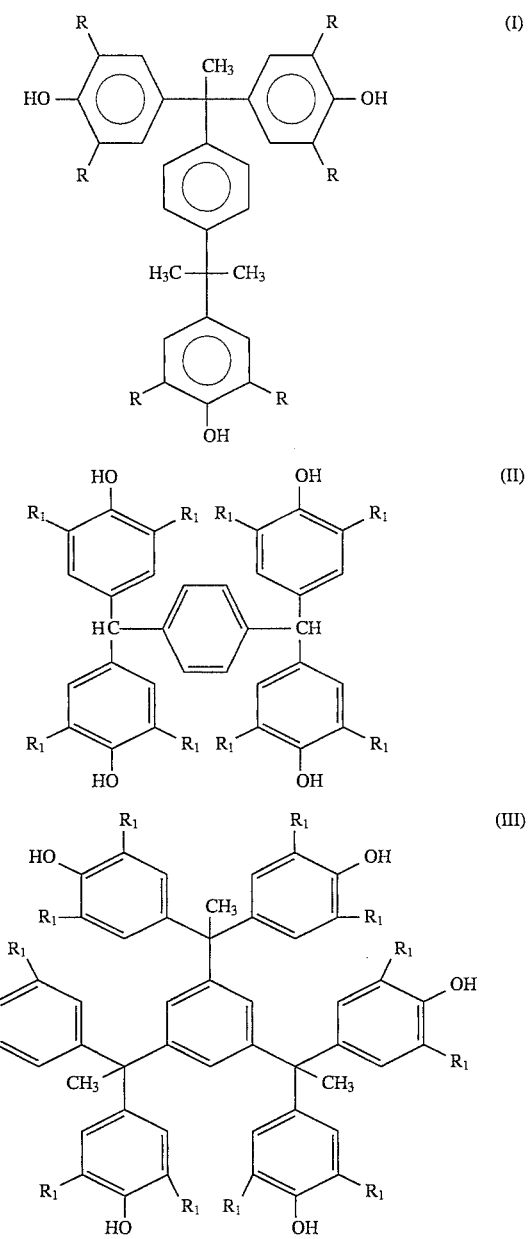

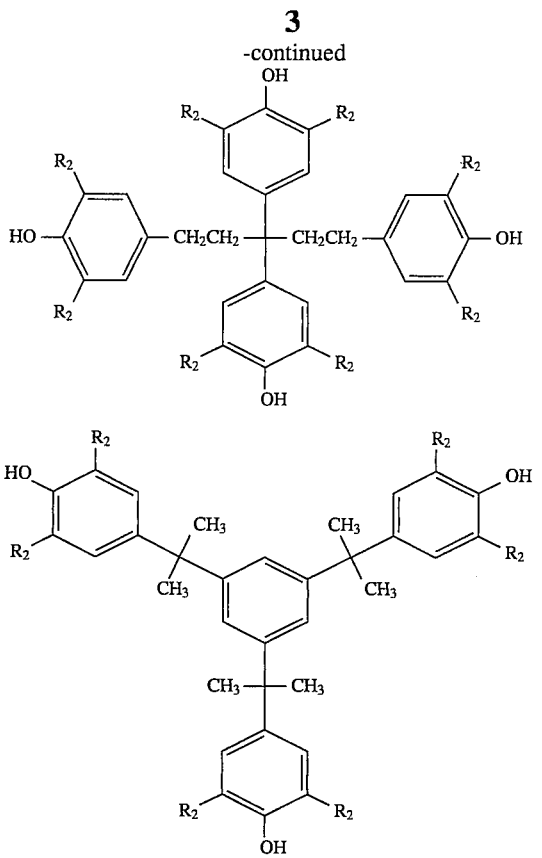

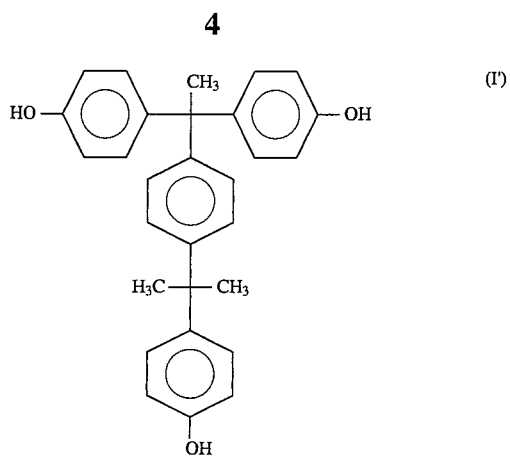

wherein each R represents $CH_2OCH_3$, $CH_2OH$, or H, provided that at least three of the R's are $CH_2OCH_3$ or $CH_2OH$, with at least one thereof being $CH_2OCH_3$;

each $R_1$ represents $CH_2OCH_3$, $CH_2OH$, or H, provided that at least two of the $R_1$'s are $CH_2OH$; and each $R_2$ represents $CH_2OCH_3$, $CH_2OH$, or H, provided that at least two of the $R_2$'S are $CH_2OH$.

DETAILED DESCRIPTION OF THE INVENTION

In the formula (I), each R represents $CH_2OCH_3$, $CH_2OH$, or H, provided that at least three of the R's are $CH_2OCH_3$ or $CH_2OH$, with at least one thereof being $CH_2OCH_3$. The compound is preferably one in which four or more of the R's are $CH_2OCH_3$ or $CH_2OH$, more preferably one in which five or more of the R's are $CH_2OCH_3$ or $CH_2OH$, and most preferably one in which all the R's are $CH_2OCH_3$ or $CH_2OH$, provided that in all cases at least one of these R's is $CH_2OCH_3$.

The methoxymethyl-containing phenol compound of this invention which is represented by formula (I) can be obtained by reacting the following phenol compound represented by formula (I') with formaldehyde in the presence of a basic catalyst and then reacting the reaction product in methanol in the presence of an acid catalyst.

The phenol compound represented by formula (I'), i.e., 4,4'-[1-[4-[2-(4-hydroxyphenyl)-2-propyl]phenyl]ethylidene]bisphenol, may be a commercially available one. Examples thereof include one commercially available under the name of "TrisP-PA" from Honshu Chemical Industry Co., Ltd. As the formaldehyde for use in this invention, either of formalin and paraformaldehyde is suitable.

In the first stage of the synthesis of a phenol compound (I) according to the present invention, the adequate range of the molar ratio of the phenol compound represented by formula (I') to formaldehyde (HCHO) to be introduced into a reactor is from 1:2 to 1:30, and preferably from 1:6 to 1:18 from the standpoint of yield.

As the basic catalyst, either of an inorganic base and an organic base is usable. Preferred examples thereof include sodium hydroxide, potassium hydroxide, lithium hydroxide, calcium hydroxide, ammonia (water), tetramethylammonium hydroxide, tetraethylammonium hydroxide, triethylamine, diethylamine, monoethylamine, trimethylamine, dimethylamine, and monomethylamine. The amount of such a basic catalyst to be used is generally from 50 to 300% by mole based on the amount of the phenol compound represented by formula (I'). Since these basic catalysts also function to dissolve the phenol compound represented by formula (I') into water, the amount thereof may be suitably increased or reduced according to the solvent to be used.

The reaction temperature is preferably from 0° to 60° C., more preferably from 0° to 45° C. At temperatures less than 0° C., the rate of the condensation reaction is low. At temperatures above 60° C., gelation takes place. The reaction time varies depending on the reaction temperature. For example, in the case of 35° C., a reaction time of 4 to 36 hours is preferred. In this case, if too long a reaction time (e.g., 48 hours or more) is used, gelation may occur.

As the acid catalyst to be used in the second stage of the synthesis of the phenol compound of this invention, any of inorganic acids such as sulfuric acid, hydrochloric acid, nitric acid, and phosphoric acid and organic acids such as benzenesulfonic acid, p-toluenesulfonic acid, and acetic acid may be employed.

The reaction temperature is preferably from 0 to 65° C., more preferably from 10° to 65° C. At temperatures less than 0° C., the reaction rate is low. The reaction time varies depending on the reaction temperature, concentration, and the amount of the acid catalyst. In the case of 65° C., for example, a reaction time of 0.5 to 36 hours is preferred.

In the formulas (II) and (III), each $R_1$ represents $CH_2OCH_3$, $CH_2OH$ or H, provided that at least two of the $R_1$'s are $CH_2OH$ group. The compound is preferably one in which five or more of the $R_1$'s are $CH_2OH$, more preferably one in which seven or more of the $R_1$'s are $CH_2OH$, and most preferably one in which all the $R_1$'s are $CH_2OH$.

In the formulas (IV) and (V), each $R_2$ represents $CH_2OCH_3$, $CH_2OH$ or H, provided that at least two of the $R_2$'s are $CH_2OH$ group. The compound is preferably one in which three or more of the $R_2$'s are $CH_2OH$, more preferably one in which five or more of the $R_2$'s are $CH_2OH$, and most preferably one in which all the $R_2$'s are $CH_2OH$.

The hydroxymethyl-containing phenol compound of this invention which is represented by formula (II), (III), (IV) or (V) can be obtained by reacting the following phenol compound represented by formulas (II'), (III'), (IV') or (V') with formaldehyde in the presence of a basic catalyst:

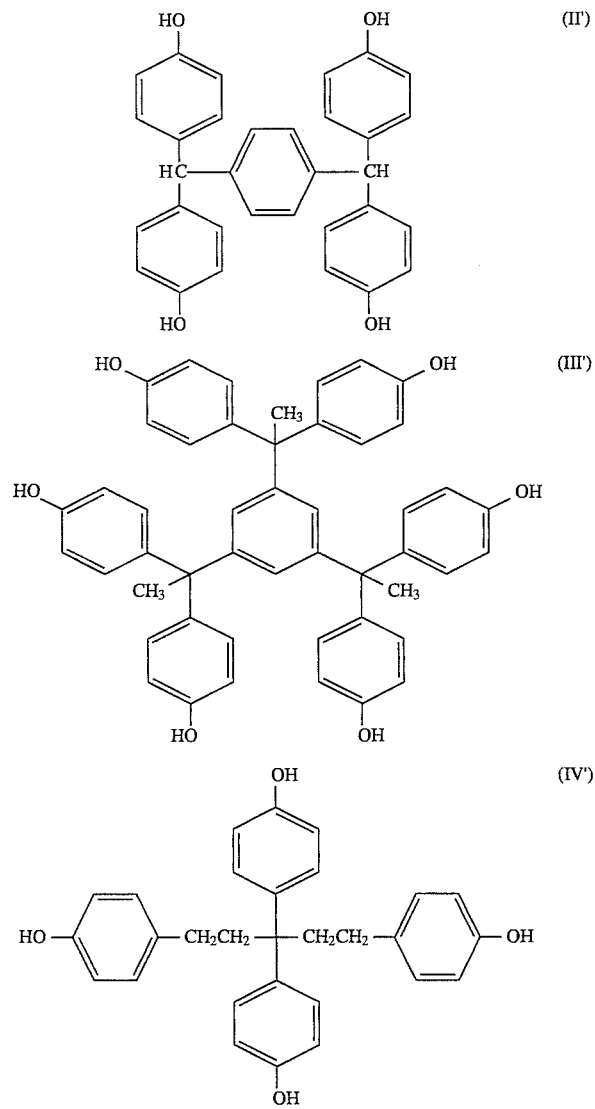

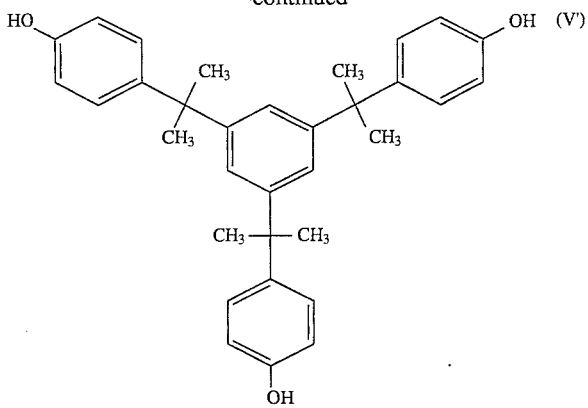

The phenol compounds represented by formula (II'), (III') or (IV') can be synthesized by the methods as described in JP-A-55-162728, JP-A-3-179353, JP-A-5-224409 and U.S. Pat. No. 5,296,330 (the term "JP-A" as used herein means an unexamined published Japanese patent application).

The phenol compound represented by formula (V') may be a commercially available one under the name of "Trisphenol-Tc" from Mitsui Petrochemical Industries, Ltd.

In the synthesis of a hydroxymethyl-containing phenol compound represented by formula (II) or (IV) according to the present invention, the adequate range of the molar ratio of the phenol compound represented by formula (II') or (IV') to formaldehyde (HCHO) to be introduced into a reactor is from 1:2 to 1:40, and preferably from 1:8 to 1:24 from the standpoint of yield. As the formaldehyde for use in this invention, either of formalin and paraformaldehyde is suitable.

As the basic catalyst, either of an inorganic base and an organic base is usable. Preferred examples thereof include sodium hydroxide, potassium hydroxide, lithium hydroxide, calcium hydroxide, ammonia (water), tetramethylammonium hydroxide, tetraethylammonium hydroxide, triethylamine, diethylamine, monoethylamine, trimethylamine, dimethylamine, and monomethylamine. The amount of such a basic catalyst to be used is generally from 50 to 600% by mole based on the amount of the phenol compound represented by formula (II') or (IV'). Since these basic catalysts also function to dissolve the phenol compound represented by formula (II') or (IV') into water, the amount thereof may be suitably increased or reduced according to the solvent to be used.

The reaction temperature is preferably from 0° to 60° C., more preferably from 10° to 45° C. At temperatures less than 10° C., the rate of the condensation reaction is low. At temperatures above 60° C., gelation takes place. The reaction time varies depending on the reaction temperature. For example, in the case of 40° C., a reaction time of 1 to 36 hours is preferred. In this case, if too long a reaction time (e.g., 48 hours or more) is used, gelation may occur. It is preferred that after completion of the reaction, neutralization with an acid be conducted. As the acid to be used, any of inorganic acids such as sulfuric acid, hydrochloric acid, nitric acid, and phosphoric acid and organic acids such as benzenesulfonic acid, p-toluenesulfonic acid, and acetic acid may be employed.

In the synthesis of a hydroxymethyl-containing phenol compound represented by formula (III) according to the present invention, the adequate range of the molar ratio of the phenol compound represented by formula (III') to formaldehyde (HCHO) to be introduced into a reactor is from 1:2 to 1:60, and preferably from 1:12 to 1:36 from the standpoint of yield. The basic catalyst to be used may be the same as that described above, but the amount thereof is preferably from 50 to 1,000% by mole based on the amount of the phenol compound represented by formula (III'). The reaction temperature and reaction time may be the same as those for the phenol compound represented by formula (II) or (IV) described above.

In the synthesis of a hydroxymethyl-containing phenol compound represented by formula (V) according to the present invention, the adequate range of the molar ratio of the phenol compound represented by formula (V') to formaldehyde (HCHO) to be introduced into a reactor is from 1:2 to 1:30, and preferably from 1:6 to 1:18 from the standpoint of yield. The basic catalyst to be used may be the same as that described above, but the amount thereof is preferably from 50 to 500% by mole based on the amount of the phenol compound represented by formula (V'). The reaction temperature and reaction time may be the same as those for the phenol compound represented by formula (II) or (IV) described above.

Specific examples of the methoxymethyl- or hydroxymethyl-containing phenol compounds of the present invention are shown below, but the present invention is not to be construed as being limited thereto.

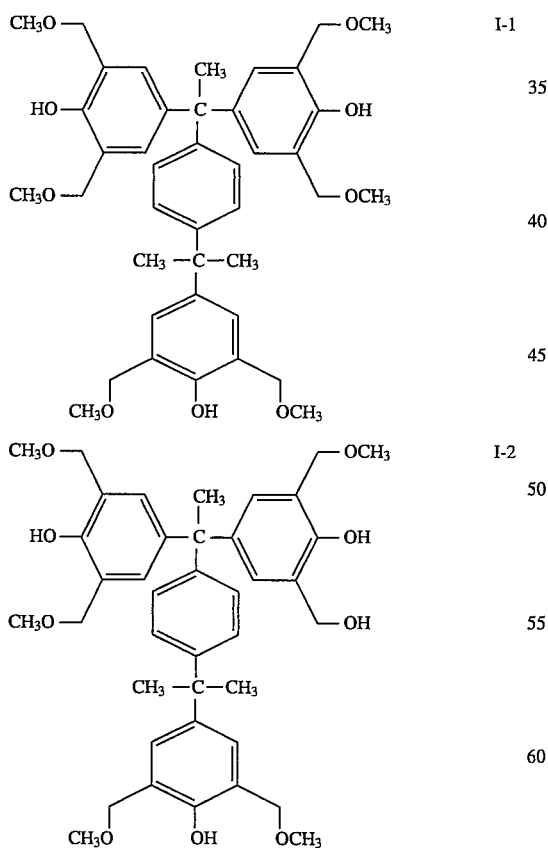

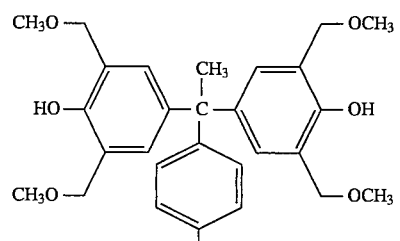

I-3

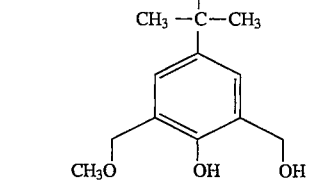

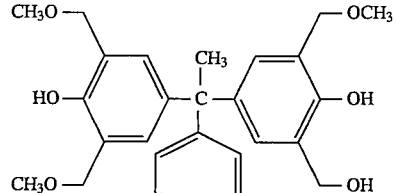

I-4

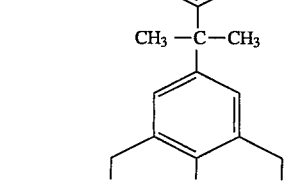

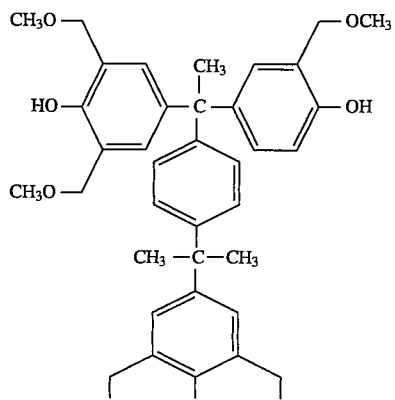

I-5

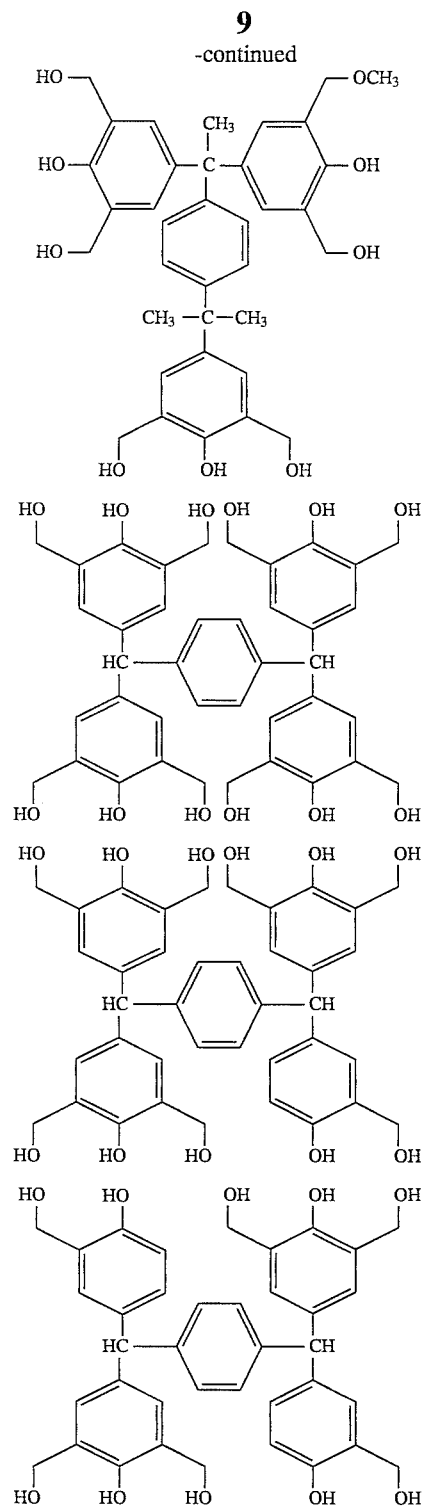
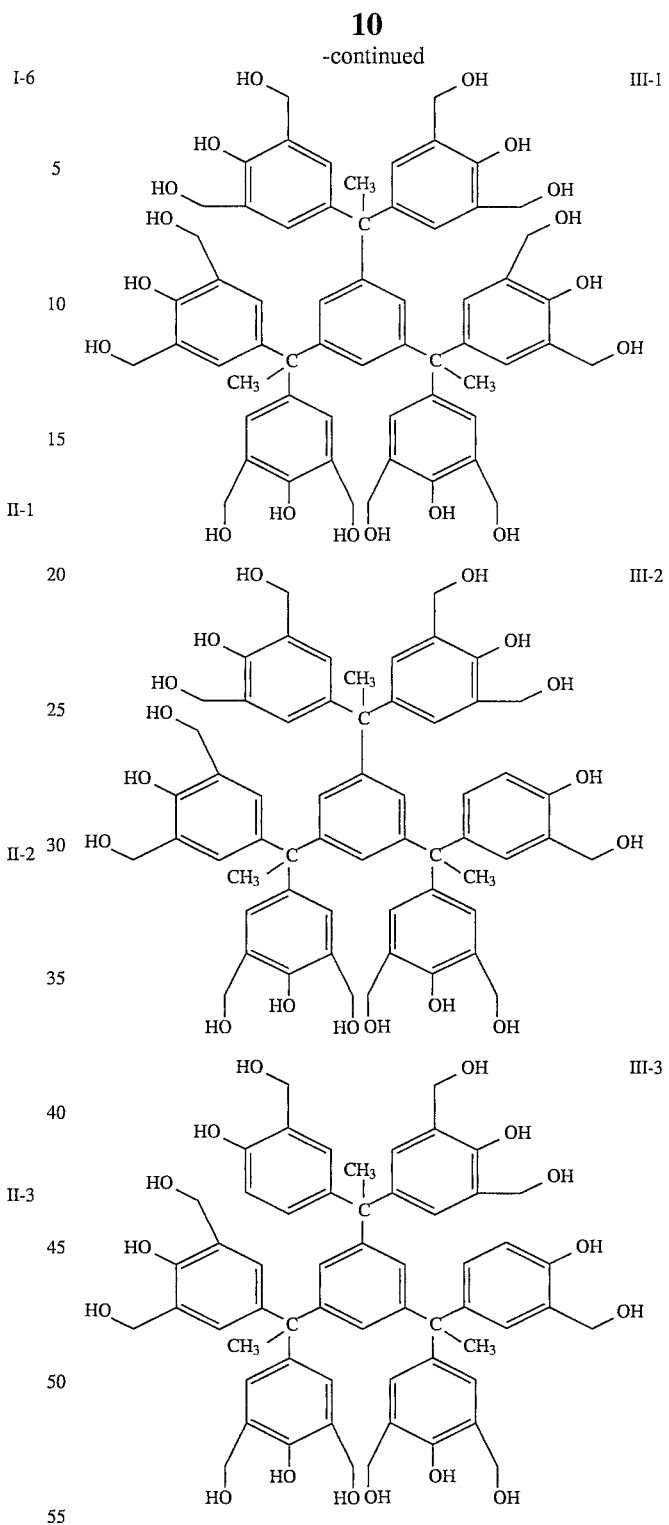

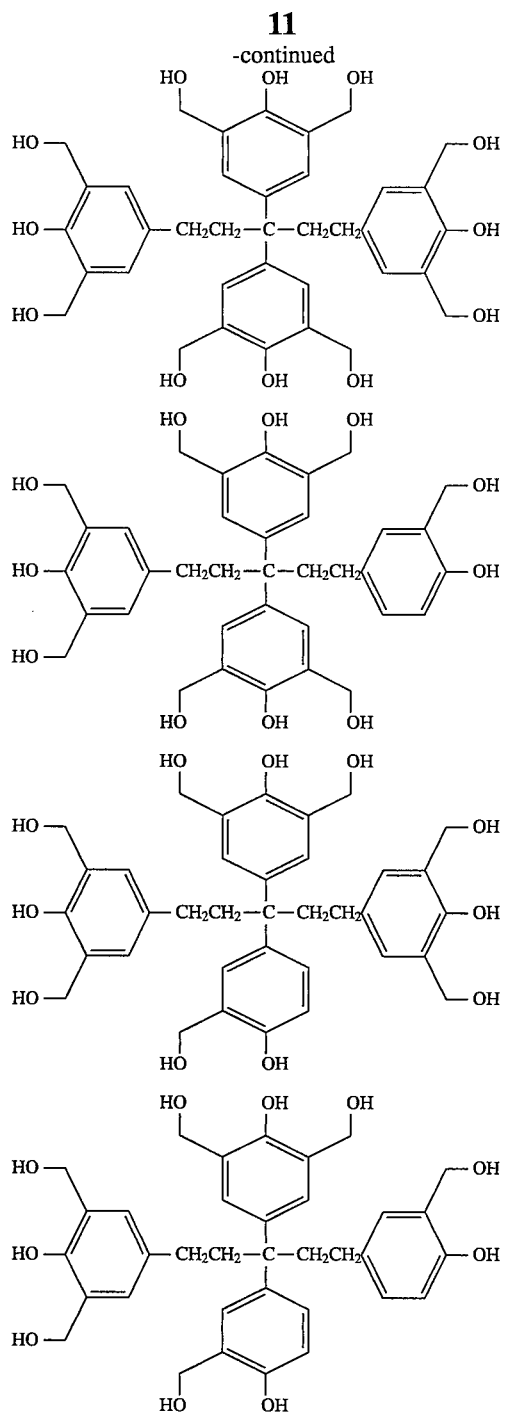
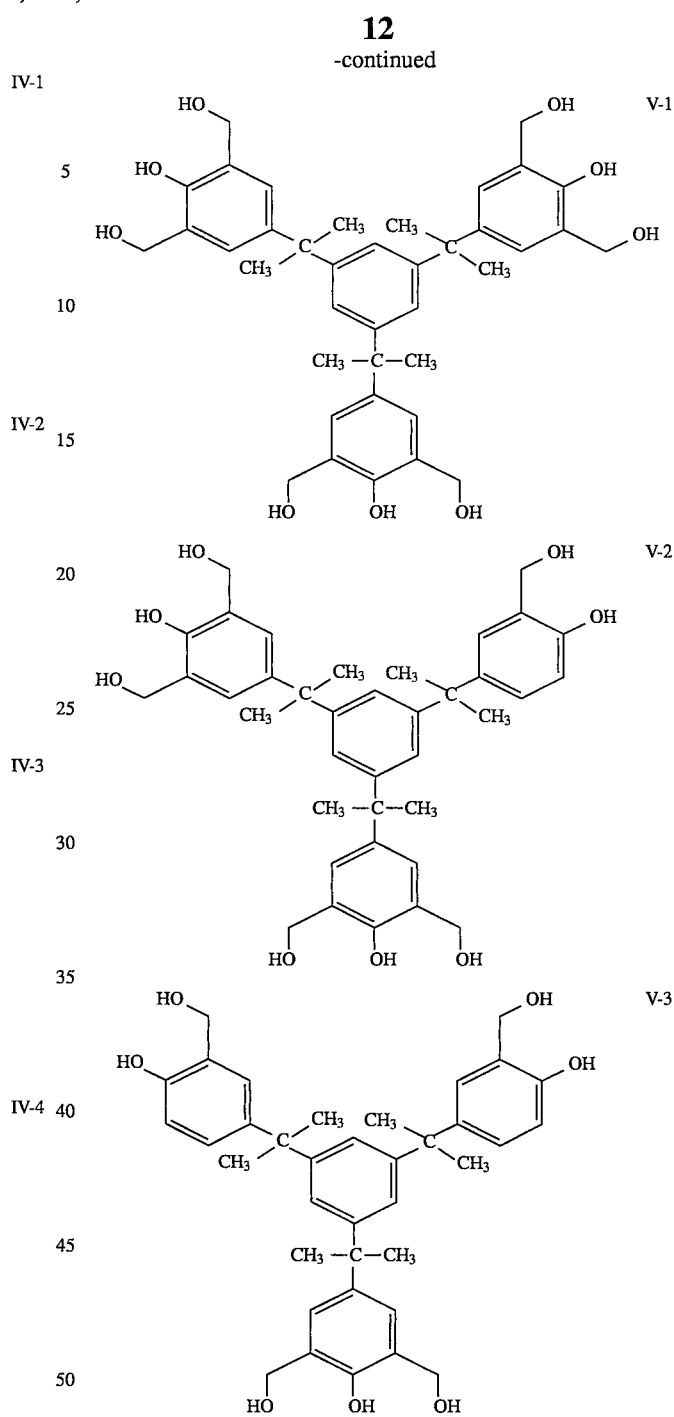

Synthesis Examples for obtaining methoxymethyl- or hydroxymethyl-containing phenol compounds (I), (II), (III), (IV) and (V) of the present invention are given below.

SYNTHESIS EXAMPLE 1

(Synthesis of Compound I-1)

Into 100 ml of aqueous potassium hydroxide solution (10%) was dissolved 20 g of the phenol compound represented by formula (I'). To this solution was dropwise added 60 ml of formalin (37%) with stirring at room temperature over a period of 1 hour. After the reaction mixture was stirred at room temperature for further 6 hours, it was poured into an aqueous solution of sulfuric acid to conduct crystallization. The pasty precipitate obtained was sufficiently washed with water and then re-crystallized with 30 ml of methanol to obtain an intermediate of the desired compound as a white powder. The amount of the thus obtained powder was 20 g.

$^1$H-NMR (DMSO-$d_6$) δ: 1.58 (s, 6H), 2.00 (s, 3H), 4.42–5.52 (m, 12H), 5.16–5.24 (m, H), 6.83–7.08 (m, 10H), 8.38 (s, 2H), 8.42 (s, 2H)

The purity was measured by reversed-phase HPLC (column, Shimpac CLC-ODS (manufactured by Shimadzu Corp.); solvent, methanol/water=60/40→90/10), and the content of the hexahydroxymethyl compound was found to be 92%.

Into 1,000 ml of methanol was then dissolved 20 g of the hexahydroxymethyl compound with heating. Thereto was added 1 ml of concentrated sulfuric acid. The reaction mixture was heated with refluxing for 12 hours. After the reaction mixture was cooled, 2 g of potassium carbonate was added and the resulting mixture was stirred and then concentrated. Thereto was added 300 ml of ethyl acetate. This mixture was washed with water and dried, and the solvent was then removed to obtain the desired compound as a colorless oily substance. The yield was 22 g.

$^1$H-NMR (CDCl$_3$) δ: 1.62 (s, 6H), 2.07 (s, 3H), 3.38 (s, 18H), 4.49 (s, 18H), 4.49 (s, 8H), 4.55 (s, 4H), 6.80 (s, 4H), 6.90 (d, 2H), 6.98 (s, 2H), 7.06 (d, 2H), 7.64 (s, 1H), 7.70 (s, 2H)

The purity was measured by reversed-phase HPLC (column, Shimpac CLC-ODS (manufactured by Shimadzu Corp.); solvent, methanol/water=60/40→90/10), and the content of the hexamethoxymethyl compound was found to be 90%.

SYNTHESIS EXAMPLE 2

(Synthesis of Compound II-1)

Into 25 ml of aqueous sodium hydroxide solution (15%) was dissolved 10 g of the phenol compound represented by formula (II'). To this solution was added 15 ml of methanol. Thereto was then dropwise added 20 g of formalin (37%) with stirring at room temperature. After completion of the dropwise addition, the reaction mixture was heated to 40° C. and stirred for further 12 hours. The resulting reaction mixture was poured into an aqueous solution of acetic acid to conduct crystallization. The solid obtained was sufficiently washed with water and then re-slurried with 100 ml of ethyl acetate to obtain 11.4 g of the desired compound as a white powder.

$^1$H-NMR (DMSO-$d_6$) δ: 4.48 (s, 16H), 5.17 (br, 8H), 5.31 (s, 2H), 6.91 (s, 8H), 7.00 (s, 4H), 8.40 (br, 4H)

The purity was measured by reversed-phase HPLC (column, Shimpac CLC-ODS (Shimadzu Corp.); solvent, methanol/water=60/40→90/10), and the content of the octakishydroxymethyl compound (the compound represented by formula (II) wherein all the $R_1$'s are CH$_2$OH, i.e., Compound II-1) was found to be 95%.

SYNTHESIS EXAMPLE 3

(Synthesis of Compound III-1)

Into a solution obtained by mixing 35 ml of aqueous sodium hydroxide solution (15%) with 25 ml of methanol was dissolved 15 g of the phenol compound represented by formula (III'). To this solution was dropwise added 33 g of formalin (37%) with stirring at room temperature. After completion of the dropwise addition, the reaction mixture was heated to 40° C. and stirred for further 20 hours. The resulting reaction mixture was poured into an aqueous solution of acetic acid. A viscous oily substance was separated from the aqueous layer by decantation, sufficiently washed with water, and then dried in a vacuum to thereby obtain 16.6 g of the desired compound as a light-yellow powder.

$^1$H-NMR (DMSO-$d_6$) δ: 1.80 (s, 9H), 4.42 (br, 24H), 6.62 (s, 3H), 6.72 (s, 12H)

The purity was measured by reversed-phase HPLC (column, Shimpac CLC-ODS (Shimadzu Corp.); solvent, methanol/water=60/40→90/10), and the content of the dodecakishydroxymethyl compound (the compound represented by formula (III) wherein all the $R_1$'s are CH$_2$OH, i.e., Compound III-1) was found to be 80%.

SYNTHESIS EXAMPLE 4

(Synthesis of Compound IV-1)

Into 40 g of aqueous sodium hydroxide solution (10%) was dissolved 11 g of the phenol compound represented by formula (IV'). To this solution was added 10 g of methanol. Thereto was then dropwise added 20 g of formalin (37%) at room temperature. After completion of the dropwise addition, the reaction mixture was heated to 40° C. and allowed to react for further 12 hours. The resulting reaction mixture was subjected to crystallization from an aqueous solution of acetic acid to obtain a white viscous solid. This white solid was sufficiently washed with water and then dried in a vacuum at room temperature. The yield was 13.6 g.

$^1$H-NMR (DMSO-$d_6$) δ: 2.11 (br, 8H), 4.47 (s, 8H), 4.48 (s, 8H), 5.19 (br, 8H), 6.84 (s, 4H), 7.00 (s, 4H), 8.40 (br, 4H)

The purity was measured by HPLC (column used, Shimpac CLC-ODS manufactured by Shimadzu Corp.), and the content of the compound represented by formula (IV) in which all the $R_2$'s are CH$_2$OH (Compound IV-1) was found to be 93%.

SYNTHESIS EXAMPLE 5

(Synthesis of Compound V-1)

Into 60 g of aqueous sodium hydroxide solution (10%) was dissolved 17.25 g of the phenol compound represented by formula (V') (as the phenol compound, use was made of one commercially available under the trade name of "TrisPhenol-Tc" from Mitsui Petrochemical Industries, Ltd). To this solution was added 15 g of methanol. Thereto was then dropwise added 30 g of formalin (37%) at room temperature. After completion of the dropwise addition, the reaction mixture was heated to 40° C. and allowed to react for further 12 hours. The resulting reaction mixture was subjected to crystallization from an aqueous solution of acetic acid to obtain a white solid. This white solid was sufficiently washed with water and then dried in a vacuum at room temperature. The yield was 19.9 g.

$^1$H-NMR (DMSO-d$_6$) δ: 1.48 (s, 18H), 4.47 (s, 12H), 5.17 (br, 6H), 6.92 (m, 9H), 8.35 (br, 3H)

The purity was measured by HPLC (column used, Shimpac CLC-ODS manufactured by Shimadzu Corp.), and the content of the compound represented by formula (V) in which all the $R_2$'s are $CH_2OH$ (Compound V-1) was found to be 90%.

The thus-obtained methoxymethyl- or hydroxymethyl-containing phenol compounds represented by formulas (I) to (V) have sufficient cured-film performances even when used in a smaller amount as compared with conventional hydroxymethyl-containing phenol compounds, and are advantageously used as a major ingredient for coating compositions, an additive for molding materials, adhesives, binders, or photosensitive printing plates, etc.

Further, the thus-obtained methoxymethyl-containing phenol compound represented by formula (I) is superior in solvent solubility to the compound represented by formula (I) wherein all the R's are $CH_2OH$ group.

Application Examples are given below.

APPLICATION EXAMPLE 1 (Lithographic Plate)

An aluminum plate (material, 1050) having a thickness of 0.3 mm was degreased by cleaning with trichloroethylene, and the surface of the resulting plate was grained with a nylon brush and an aqueous suspension of a 400-mesh pumice and then sufficiently washed with water. This plate was etched by immersing it in a 45° C. 25% aqueous sodium hydroxide solution for 9 seconds and then washed with water. Subsequently, the plate was further immersed in 20% nitric acid for 20 seconds and then washed with water. The aluminum amount thus removed from the grained surface by etching was about 3 g/m². The resulting plate was subjected to direct-current anodizing at a current density of 15 A/dm² using 7% sulfuric acid as the electrolytic solution to deposit an oxide film on the plate in an amount of 3 g/m², and was then washed with water and dried. This aluminum plate was subsequently coated with the primer specified below and dried at 80° C. for 30 seconds. The amount of the primer coat after drying was 10 mg/m².

| (Primer) | |
|---|---|
| β-Alanine | 0.1 g |
| Phenylphosphonic acid | 0.05 g |
| Methanol | 40 g |
| Pure water | 60 g |

Further, the photosensitive solutions specified below were applied on the resulting aluminum plate and the coatings were dried at 100° C. for 2 minutes to obtain positive photosensitive lithographic plates. The amount of the coating after drying was 1.8 g/m² for all the photosensitive solutions.

| Photosensitive Solution (unit; gram) | |
|---|---|
| Product of esterification of naphthoquinone-1,2-diazide-5-sulfonic acid chloride with a pyrogallol-acetone resin | 0.90 |
| Cresol-formaldehyde novolak (as shown in Table 1) (meta:para ratio = 6:4; weight-average molecular weight, 1,800; unreacted cresol content, 0.5%) | |
| p-Octylphenol-formaldehyde novolak | 0.02 |
| Naphthoquinone-1,2-diazide-5-sulfonic acid chloride | 0.01 |
| Phenol derivative (as shown in Table 1) | |
| Tetrahydrophthalic anhydride | 0.05 |
| 4-(p-N,N-diethoxycarbonylaminophenyl)-2,6-bis(trichloromethyl)-s-triazine | 0.02 |
| 4-(p-N-(p-Hydroxybenzoyl)aminophenyl)-2,6-bis(trichloromethyl)-s-triazine | 0.02 |
| Dye obtained from Victoria Pure Blue BOH by converting the counter ion into 1-naphthalenesulfonic acid | 0.03 |
| MEGAFAC F-177 (fluorine compound surfactant manufactured by Dainippon Ink and Chemicals Inc.) | 0.15 |
| Methyl ethyl ketone | 26 |

TABLE 1

| Lithographic plate | Amount of cresol-formaldehyde novolak used (g) | Phenol derivative Formula | Amount used (g) |
|---|---|---|---|
| [A] | 2.10 | methoxymethylphenol compound (I-1) | 0.06 |
| [B] | 2.16 | none | — |

These positive photosensitive lithographic plates were exposed to the light from a 30-ampere carbon arc lamp placed at a distance of 70 cm therefrom, and were then subjected to automatic development (by means of "800U," an automatic developing machine manufactured by Fuji Photo Film Co., Ltd.) at 25° C. for 40 seconds with DP-4 (trade name; manufactured by Fuji Photo Film Co., Ltd.) diluted 8 times. The proper exposure time for this treatment was the period in which the part corresponding to step 5 on a gray scale having a density difference of 0.15 (manufactured by Fuji Photo Film Co., Ltd.) became completely clear, and this exposure time was taken as the sensitivity of the photosensitive lithographic plate. Further, the time required for the part corresponding to the solid step on the gray scale to undergo a two-step color change therefrom in 40-second tray development with 25° C. DP-4 diluted 8 times was determined (this time being hereinafter referred to as "development acceptability").

The results of the sensitivity (exposure time) and development acceptability evaluations of these positive photosensitive lithographic plates are shown in Table 2.

These photosensitive lithographic plates were then placed on a transparent base and exposed for 60 seconds in a vacuum frame through a positive original film using a halide lamp as a light source. The resulting plates were subsequently processed by passing these through an automatic developing machine containing developing solution DP-4 (1:8) and rinsing solution FR-3 (1:7) manufactured by Fuji Photo Film Co., Ltd. Thereafter, the plate surfaces were wiped with burning conditioner BC-3 manufactured by Fuji Photo Film Co., Ltd., and processed for 7 minutes with burning device BP-1300. The plate surfaces were subsequently treated with a liquid prepared by diluting gum GU-7 manufactured by Fuji Photo Film Co., Ltd. with water 2 times, allowed to stand for 1 day, and then subjected to printing with printing machine Heidel KOR-D. The burning temperature, the number of prints obtained, and the degree of spreading in a halftone image area are shown in Table 2.

TABLE 2

| | | | Burning temperature | | | |
|---|---|---|---|---|---|---|
| | | | 200° C. | | 260° C. | |
| Litho-graphic plate | Sensi-tivity (expo-sure) time) (sec) | Devel-opment accept-ability (min) | Impression capacity (× 10,000 sheets) | Degree of spread-ing in halftone image area | Impression capacity (× 10,000 sheets) | Degree of spread-ing in halftone image area |
| [A] | 40 | 6 | 25 | A | 40 | B |
| [B] | 60 | 7 | 15 | C | 20 | D |

Degree of spreading in halftone image area:
A: Completely no spreading
B: Almost no spreading
C: Spreading occurred
D: Considerable spreading occurred The results summarized in Table 2 show that as compared with the lithographic plate [B] containing no phenol derivative, the lithographic plate [A] containing a phenol derivative of the present invention is almost free from scumming of non-image area and has improved impression capacity even when burning is performed at any temperature.

Furthermore, the lithographic plate [A] containing a phenol derivative of the present invention has higher sensitivity (is shorter in proper exposure time) than the lithographic plate [B], and the development acceptability thereof is on a level with no practical problems.

The above demonstrates that the phenol derivative of the present invention not only enhances sensitivity without causing a significant decrease in development acceptability, but also greatly diminishes the scumming of non-image area which is caused by burning, even at any temperature, and improves impression capacity. Thus, the derivative of the invention has exceedingly high performances.

APPLICATION EXAMPLE 2 (Photoresist)

A photosensitive solution [C] having the following composition was prepared.

| Photosensitive Solution [C] | |
|---|---|
| Cresol-formaldehyde novolak resin (meta/para ratio = 6:4) | 1.0 g |
| Compound (I) of this invention, I-1 | 0.1 g |
| Triphenylsulfonium trichloromethane-sulfonate | 20 mg |
| Ethyl Cellosolve acetate | 10 ml |

A comparative photosensitive solution [D] was prepared separately which was the same as [C] above except that 0.1 g of bishydroxymethyl-p-cresol was used in place of the compound (I) of this invention.

The photosensitive solutions [C] and [D] described above were applied on a silicon wafer with a spinner and dried on a hot plate at 90° C for 2 minutes.

The resulting coatings were exposed using a g-line stepper (436 nm) and developed with a 2.4% aqueous solution of tetramethylammonium hydroxide to thereby obtain resists having a 0.48-μm line-and-space pattern.

The resist obtained from the photosensitive solution [D] had a sensitivity of 170 mJ/cm$^2$, whereas the resist obtained from the photosensitive solution [C] had a sensitivity of 100 mJ/cm$^2$. This shows that the resist obtained using the compound (I) of this invention has high sensitivity.

APPLICATION EXAMPLE 3 (Coating Composition)

A coating fluid [E] was prepared by dissolving 10 g of the compound represented by formula (I) which had been obtained in Synthesis Example 1 and 90 g of a phenol-formaldehyde-resol resin into 350 ml of a methanol-acetone-butyl alcohol (8:1:1) mixed solvent. Likewise, a coating fluid [F] was prepared by dissolving 10 g of bishydroxymethyl-p-cresol in place of the compound (I) and 90 g of a phenol-formaldehyde-resol resin into 350 ml of the same mixed solvent as the above-described one. Each of the coating fluids [E] and [F] was applied on a wood plate after a 50% methanol solution of benzenesulfonic acid was added thereto as a hardener in an amount of 15% based on the weight of the coating fluid.

After the coated samples were then allowed to stand at room temperature for 1 week, they were immersed in methanol and the film surfaces were visually examined.

As a result, the surface of the sample obtained using the coating fluid [F] had suffered blushing, whereas the sample obtained using the coating fluid [E] had not changed, showing that the compound (I) of the present invention has the effect of improving the solvent resistance of coating fluids.

Acid resistance and alkali resistance were evaluated likewise based on immersion in 50% acetic acid and in 5% aqueous sodium hydroxide solution, respectively. As a result, the coating film formed from the coating fluid [E] showed higher acid and alkali resistance than the coating film formed from the coating fluid [F].

APPLICATION EXAMPLE 4 (Lithographic Plate)

An aluminum plate (material, 1050) having a thickness of 0.3 mm was degreased by cleaning with trichloroethylene, and the surface of the resulting plate was grained with a nylon brush and an aqueous suspension of a 400-mesh pumice and then sufficiently washed with water. This plate was etched by immersing it in a 45° C. 25% aqueous sodium hydroxide solution for 9 seconds and then washed with water. Subsequently, the plate was further immersed in 20% nitric acid for 20 seconds and then washed with water. The aluminum amount thus removed from the grained surface by etching was about 3 g/m$^2$. The resulting plate was subjected to direct-current anodizing at a current density of 15 A/dm$^2$ using 7% sulfuric acid as the electrolytic solution to deposit an oxide film on the plate in an amount of 3 g/m$^2$, and was then washed with water and dried. This aluminum plate was subsequently coated with the primer specified below and dried at 80° C. for 30 seconds. The amount of the primer coat after drying was 10 mg/m$^2$.

| (Primer) | |
|---|---|
| β-Alanine | 0.1 g |
| Phenylphosphonic acid | 0.05 g |
| Methanol | 40 g |
| Pure water | 60 g |

Further, the photosensitive liquids specified below were applied on the resulting aluminum plate and the coatings were dried at 100° C. for 2 minutes to obtain positive photosensitive lithographic plates. The amount of the coating after drying was 1.8 g/m$^2$ for all the photosensitive solutions.

| Photosensitive Solution (unit; gram) | |
|---|---|
| Product of esterification of naphthoquinone-1,2-diazide-5-sulfonic acid chloride with a pyrogallol-acetone resin | 0.90 |
| Cresol-formaldehyde novolak (as shown in Table 3) (meta:para ratio = 6:4; weight-average molecular weight, 1,800; unreacted cresol content, 0.5%) | |
| p-Octylphenol-formaldehyde novolak | 0.02 |
| Naphthoquinone-1,2-diazide-5-sulfonic acid chloride | 0.01 |
| Phenol derivative (as shown in Table 3) | |
| Tetrahydrophthalic anhydride | 0.05 |
| 4-(p-N,N-bis(ethoxycarbonylmethyl)phenyl)-2,6-bis(trichloromethyl)-s-triazine | 0.02 |
| 4-(p-N-(p-Hydroxybenzoyl)aminophenyl)-2,6-bis(trichloromethyl)-s-triazine | 0.02 |
| Dye obtained from Victoria Pure Blue BOH by converting the counter ion into 1-naphthalenesulfonic acid | 0.03 |
| MEGAFAC F-177 (fluorine compound surfactant manufactured by Dainippon Ink and Chemicals Inc.) | 0.15 |
| Methyl ethyl ketone | 25 |
| Methanol | 1 |

TABLE 3

| Lithographic plate | Amount of cresol-formaldehyde novolak used (g) | Phenol derivative Formula | Amount used (g) |
|---|---|---|---|
| [G] | 2.1 | hydroxymethylphenol compound (II-1) | 0.06 |
| [H] | 2.0 | hydroxymethylphenol compound (III-1) | 0.06 |
| [I] | 2.1 | none | — |

With respect to these positive photosensitive lithographic plates, the sensitivity (exposure time), the development acceptability, the burning temperature, the number of prints obtained, and the degree of spreading in a halftone image area were examined in the same manner as in Application Example 1.

The results are shown in Table 4 below.

TABLE 4

| | | | Burning temperature | | | |
|---|---|---|---|---|---|---|
| | | | 200° C. | | 260° C. | |
| Lithographic plate | Sensitivity (exposure time) (sec) | Development acceptability (min) | Impression capacity (× 10,000 sheets) | Degree of spreading in halftone image area | Impression capacity (× 10,000 sheets) | Degree of spreading in halftone image area |
| [G] | 40 | 6 | 25 | A | 30 | B |
| [H] | 38 | 6 | 22 | A | 25 | B |
| [I] | 60 | 7 | 15 | C | 20 | D |

Degree of spreading in halftone image area:
A: Completely no spreading
B: Almost no spreading
C: Spreading occurred
D: Considerable spreading occurred The results summarized in Table 4 show that as compared with the lithographic plate [I] containing no phenol derivative, the lithographic plates [G] and [H] containing phenol derivatives of the present invention are almost free from scumming of non-image area and have improved impression capacity even when burning is performed at any temperature.

Furthermore, the lithographic plates [G] and [H] containing phenol derivatives of the present invention have higher sensitivity (are shorter in proper exposure time) than the lithographic plate [I]. Although the plates [G] and [H] are slightly inferior to the plate [C] in development acceptability, the development acceptability of the former plates is on a level with no practical problems.

The above demonstrates that the phenol derivatives of the present invention not only enhance sensitivity without causing a significant decrease in development acceptability, but also greatly diminish the scumming of non-image area which is caused by burning, even at any temperature, and improve impression capacity. Thus, the derivatives of the invention have exceedingly high performances.

APPLICATION EXAMPLE 5 (Photoresist)

A photosensitive solution [J] having the following composition was prepared.

| Photosensitive Solution [J] | |
|---|---|
| Cresol-formaldehyde novolak resin (meta/para ratio = 6:4) | 1.0 g |
| Compound (II) of this invention, II-1 | 0.1 g |
| Triphenylsulfonium trichloromethane-sulfonate | 20 mg |
| Ethyl Cellosolve acetate | 10 ml |

A comparative photosensitive solution [K] was prepared separately which was the same as [J] above except that 0.1 g of bishydroxymethyl-p-cresol was used in place of the compound (II) of this invention.

The photosensitive solutions [J] and [K] described above were applied on a silicon wafer with a spinner and dried on a hot plate at 90° C. for 2 minutes.

The resulting coatings were exposed using a g-line stepper (436 nm) and developed with a 2.4% aqueous solution of tetramethylammonium hydroxide to thereby obtain resists having a 0.48-μm line-and-space pattern.

The resist obtained from the photosensitive solution [K] had a sensitivity of 170 mJ/cm$^2$, whereas the resist obtained from the photosensitive solution [J] had a sensitivity of 120 mJ/cm$^2$. This shows that the resist obtained using the compound (II) of this invention has high sensitivity.

APPLICATION EXAMPLE 6 (Lithographic Plate)

An aluminum plate (material, 1050) having a thickness of 0.3 mm was degreased by cleaning with trichloroethylene, and the surface of the resulting plate was grained with a nylon brush and an aqueous suspension of a 400-mesh pumice and then sufficiently washed with water. This plate was etched by immersing it in a 45° C. 25% aqueous sodium hydroxide solution for 9 seconds and then washed with water. Subsequently, the plate was further immersed in 20% nitric acid for 20 seconds and then washed with water. The aluminum amount thus removed from the grained surface by etching was about 3 g/m$^2$. The resulting plate was subjected to direct-current anodizing at a current density of 15 A/dm$^2$ using 7% sulfuric acid as the electrolytic solution to deposit an oxide film on the plate in an amount of 3 g/m$^2$, and was then washed with water and dried. This aluminum plate was subsequently coated with the primer specified below and dried at 80° C. for 30 seconds. The amount of the primer coat after drying was 10 mg/m$^2$.

| (Primer) | |
|---|---|
| β-Alanine | 0.1 g |
| Phenylphosphonic acid | 0.05 g |
| Methanol | 40 g |
| Pure water | 60 g |

Further, the photosensitive solutions specified below were applied on the resulting aluminum plate and the coatings were dried at 100° C. for 2 minutes to obtain positive photosensitive lithographic plates. The amount of the coating after drying was 1.8 g/m$^2$ for all the photosensitive solutions.

| Photosensitive Solution (unit; gram) | |
|---|---|
| Product of esterification of naphthoquinone-1,2-diazide-5-sulfonic acid chloride with a pyrogallol-acetone resin | 0.90 |
| Cresol-formaldehyde novolak (meta:para ratio = 6:4; weight-average molecular weight, 1,800; unreacted cresol content, 0.5%) | (as shown in Table 5) |
| p-Octylphenol-formaldehyde novolak | 0.02 |
| Naphthoquinone-1,2-diazide-5-sulfonic acid chloride | 0.01 |
| Phenol derivative | (as shown in Table 5) |
| Tetrahydrophthalic anhydride | 0.05 |
| [furan-CH=CH-triazine-(CCl$_3$)$_2$ structure] | 0.02 |
| [methylfuran-CH=CH-triazine-(CCl$_3$)$_2$ structure] | 0.02 |
| Dye obtained from Victoria Pure Blue BOH by converting the counter ion into 1-naphthalenesulfonic acid | 0.03 |
| MEGAFAC F-177 (fluorine compound surfactant manufactured by Dainippon Ink and Chemicals Inc.) | 0.15 |
| Methyl ethyl ketone | 25 |
| Methanol | 1 |

TABLE 5

| Lithographic plate | Amount of cresol-formaldehyde novolak used (g) | Phenol derivative Formula | Amount used (g) |
|---|---|---|---|
| [L] | 2.1 | hydroxymethylphenol compound (IV-1) | 0.06 |
| [M] | 2.0 | hydroxymethylphenol compound (V-1) | 0.06 |
| [N] | 2.1 | none | — |

With respect to these positive photosensitive lithographic plates, the sensitivity (exposure time), the development acceptability, the burning temperature, the number of prints obtained, and the degree of spreading in a halftone image area were examined in the same manner as in Application Example 1.

The results are shown in Table 6 below.

TABLE 6

| Lithographic plate | Sensitivity (exposure time) (sec) | Development acceptability (min) | Burning temperature | | | |
|---|---|---|---|---|---|---|
| | | | 200° C. | | 260° C. | |
| | | | Impression capacity (× 10,000 sheets) | Degree of spreading in halftone image area | Impression capacity (× 10,000 sheets) | Degree of spreading in halftone image area |
| [L] | 40 | 6 | 22 | A | 28 | B |
| [M] | 38 | 6 | 22 | A | 28 | B |
| [N] | 60 | 7 | 15 | C | 20 | D |

Degree of spreading in halftone image area:
A: Completely no spreading
B: Almost no spreading
C: Spreading occurred
D: Considerable spreading occurred The results summarized in Table 6 show that as compared with the lithographic plate [N] containing no phenol derivative, the lithographic plates [L] and [M] containing phenol derivatives of the present invention are almost free from scumming of non-image area and have improved impression capacity even when burning is performed at any temperature.

Furthermore, the lithographic plates [L] and [M] containing phenol derivatives of the present invention have higher sensitivity (are shorter in proper exposure time) than the lithographic plate [N]. Although the plates [L] and [M] are slightly inferior to the plate [C] in development acceptability, the development acceptability of the former plates is on a level with no practical problems.

The above demonstrates that the phenol derivatives of the present invention not only enhance sensitivity without causing a significant decrease in development acceptability, but also greatly diminish the scumming of non-image area which is caused by burning, even at any temperature, and improve impression capacity. Thus, the derivatives of the invention have exceedingly high performances.

APPLICATION EXAMPLE 7 (Photoresist)

Photosensitive solutions [O], [P], and [Q] having the following compositions were prepared.

| Photosensitive Solution | |
|---|---|
| Cresol-formaldehyde novolak resin (meta/para ratio = 6:4) | 1.0 g |
| Phenol derivative (as shown in Table 7) | |
| Triphenylsulfonium trichloromethane-sulfonate | 20 mg |
| Ethyl Cellosolve acetate | 10 ml |

TABLE 7

| Photosensitive solution | Phenol derivative | Amount used | Sensitivity |
|---|---|---|---|
| [O] | hydroxymethylphenol compound (IV-1) | 0.1 g | 120 mJ |
| [P] | hydroxymethylphenol compound (V-1) | 0.1 g | 110 mJ |
| [Q] | bishydroxymethyl-p-cresol | 0.1 g | 170 mJ |

The photosensitive solutions [O], [P], and [Q] described above were applied on a silicon wafer with a spinner and dried on a hot plate at 90° C. for 2 minutes.

The resulting coatings were exposed using a g-line stepper (436 nm) and developed with a 2.4% aqueous solution of tetramethylammonium hydroxide to thereby obtain resists having a 0.48-μm line-and-space pattern.

The results summarized in Table 7 show that the resists obtained using the compounds (IV) and (V) of this invention have high sensitivity.

While the invention has been described in detail and with reference to specific embodiments thereof, it will be apparent to one skilled in the art that various changes and modifications can be made therein without departing from the spirit and scope thereof.

What is claimed is:

1. A methoxymethyl-containing phenol compound represented by the following formula (I):

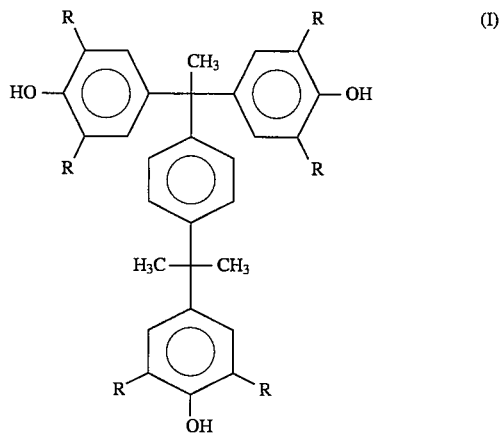

wherein each R represents $CH_2OCH_3$, $CH_2OH$, or H, provided that at least three of the R's are $CH_2OCH_3$ or $CH_2OH$, with at least one thereof being $CH_2OCH_3$.

2. A hydroxymethyl-containing phenol compound represented by the following formula (II) or (III):

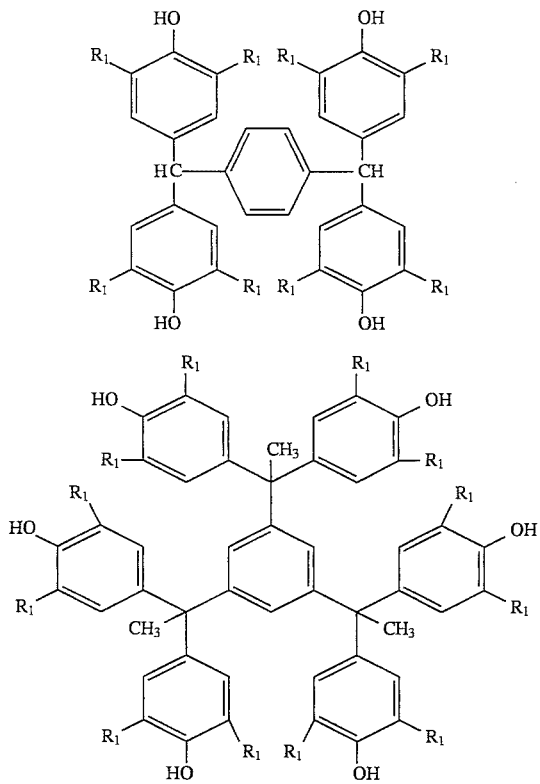

(II)

(III)

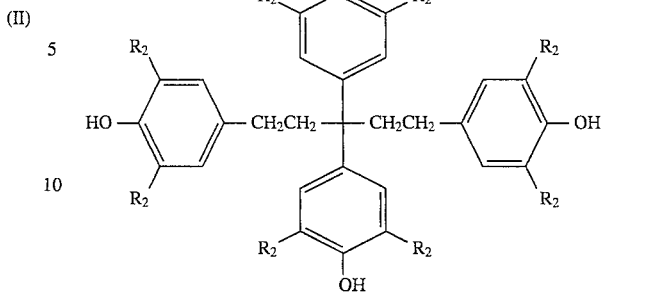

(IV)

wherein each $R_2$ represents $CH_2OCH_3$, $CH_2OH$ or H, provided that at least two of the $R_2$'s are $CH_2OH$.

5. A hydroxymethyl-containing phenol compound represented by the following formula (V):

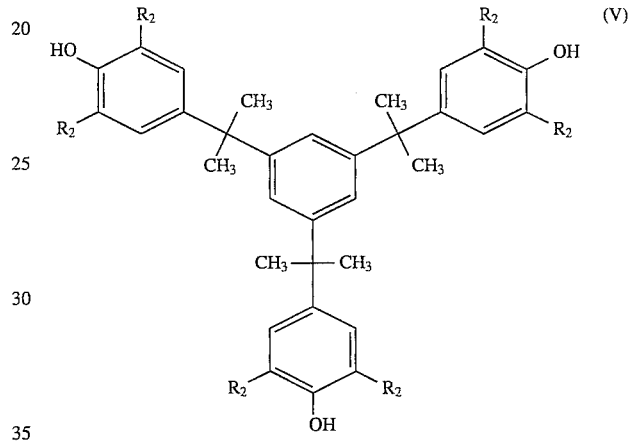

(V)

wherein each $R_2$ represents $CH_2OCH_3$, $CH_2OH$ or H, provided that at least two of the $R_2$'s are $CH_2OH$.

wherein each $R_1$ represents $CH_2OCH_3$, $CH_2OH$ or H, provided that at least two of the $R_1$'s are $CH_2OH$.

3. A compound as claimed in claim 2, wherein all the $R_1$'s are $CH_2OH$.

4. A hydroxymethyl-containing phenol compound represented by the following formula (IV):

* * * * *